United States Patent [19]

France et al.

[11] Patent Number: 5,275,823
[45] Date of Patent: Jan. 4, 1994

[54] PHARMACEUTICAL COMPOSITIONS

[75] Inventors: Gordon France, Digswell, England; Graham S. Leonard, St. Albans, Great Britain

[73] Assignee: Smith Kline & French Laboratories Ltd., Welwyn Garden City, United Kingdom

[21] Appl. No.: 812,531

[22] Filed: Dec. 23, 1991

Related U.S. Application Data

[63] Continuation of Ser. No. 344,192, Apr. 27, 1989, abandoned.

[51] Int. Cl.$^5$ .......................... A61K 9/16; A61K 9/20
[52] U.S. Cl. .................................... 424/489; 424/464; 424/465; 424/441; 514/772.3; 514/778; 514/781
[58] Field of Search ................ 424/489, 464, 465, 441

[56] References Cited

U.S. PATENT DOCUMENTS 4,327,076  4/1982  Puglia et al. ........................ 424/441
4,800,087  1/1989  Mehta ................................. 424/482
4,824,664  4/1989  Tarral et al. ....................... 424/446
4,828,836  5/1989  Elger et al. ......................... 424/464

FOREIGN PATENT DOCUMENTS 1229552 11/1987  Canada .
0003589  8/1979  European Pat. Off. .
0273005  6/1988  European Pat. Off. .
2175853 10/1973  France .
2197592  3/1974  France .
0067375  5/1980  Japan .

*Primary Examiner*—Paul R. Michl
*Assistant Examiner*—James M. Spear
*Attorney, Agent, or Firm*—Dara L. Dinner; Stephen Venetianer; Edward T. Lentz

[57] ABSTRACT

Chewable tablets containing unpleasant tasting medicaments such as cimetidine are provided. The palatability of the tablets is improved by including certain hygroscopic water-insoluble substances as extragranular excipients in amounts corresponding to 5% (w/w) to 15% (w/w) of the table.

17 Claims, No Drawings

PHARMACEUTICAL COMPOSITIONS

This is a continuation of application Ser. No. 07/344,192 filed Apr. 27, 1989, now abandoned.

The present invention relates to solid pharmaceutical compositions such as chewable tablets, particularly those containing histamine $H_2$-receptor antagonists such as cimetidine, and to methods for preparing such compositions.

Chewable tablets are often employed when the active ingredient is intended to act in a localized manner, rather than systemically. For example, antacids are often administered in chewable tablet form. Chewable tablets can also be employed as an alternative to administering a number of smaller tablets when the active ingredient requires a relatively large dose in order to achieve the desired therapeutic effect. A further reason for using chewable tablets, as distinct from tablets which are intended to be swallowed intact, is to enable the tablet to be reduced to a finely divided state quickly, thereby facilitating more rapid release and hence more rapid absorption of the active ingredients. Chewable tablets can thus be useful for the treatment of conditions where a quick onset of action of the active ingredient is required. One such condition is gastrooesophageal reflux disease (GORD) in which quick control of gastric acidity is desirable in order to minimise the adverse effects of acid reflux. Histamine $H_2$-receptor antagonists, such as cimetidine, have been shown, or would be expected, to be useful in the treatment of GORD, and the provision of a chewable tablet containing such $H_2$-antagonists represents one object of the present invention.

It is generally recognized (see, for example, EP 0190826) that patient compliance with a drug treatment regimen can be a problem when the drug has an unpleasant taste or mouth feel and this has prompted numerous investigations into methods of improving palatability.

The provision of palatable dosage forms represents a particular problem when the dosage form is a chewable tablet, i.e. a tablet intended to disintegrate in the mouth under the action of chewing or sucking and where, in consequence, the unpleasant-tasting active ingredient has ample opportunity to come into contact with the bitter-taste receptors on the tongue.

One known approach to the solution of this problem is to coat the drug with a coating agent which prevents it from coming into contact with the taste-buds. Such an approach can have certain drawbacks; firstly the coating agent may be removed by the mechanical grinding action of the teeth during chewing; and secondly the presence of a substantial layer of coating agent can inhibit release of the drug in the gastrointestinal tract and thereby lower its bioavailability.

A further known approach is to adsorb the drug onto a suitable substrate thereby also preventing contact of the drug with the taste-buds. This approach is described in US Pat. No. 4,647,459.

European patent Application 0190826 describes a method for masking the unpleasant taste of a substance by forming the unpleasant-tasting substance into an aggregate along with a pre-swelled substantially anhydrous hydrocolloid. The hydrocolloid absorbs saliva and acquires a slippery texture which enables it to lubricate the particles of aggregate and mask the unpleasant gritty texture of drugs such as cholestyramine, and dietary fiber supplements such as locust bean gum. The preparation of the aggregates involves preparing an aqueous composition of the hydrocolloid, contacting the aqueous composition with the unpleasantly textured substance to form the aggregates, followed by drying the aggregates. The preferred and exemplified method of preparing such an aggregate involves the use of fluidized bed granulator.

The above-mentioned methods of masking the unpleasant tastes and textures of certain medicaments involve incorporating the medicament into the aggregate or granule.

It has now been found that the unpleasant tastes of certain medicaments, for example the intensely bitter taste of histamine $H_2$-receptor antagonists such as cimetidine, can be reduced or eliminated by employing a water-insoluble hygroscopic excipient such as microcrystalline cellulose in a particular amount as an extragranular excipient.

The use of extragranular microcrystalline cellulose in a solid dosage form is described in EP 0196546. However, the particular use described in EP 0196546 is use as a cushioning agent between coated granules to prevent fracturing of the granule-coating during a compression step. No mention is made of any taste-masking properties nor is it suggested that such dosage forms could be in the form of chewable tablets.

In a first aspect, the present invention provides a pharmaceutical chewable tablet comprising:
(i) granules containing a therapeutically active substance; and
(ii) an extragranular water-insoluble hygroscopic excipient in an amount of 5% to 15% by weight of the total weight of the tablet.

Chewable tablets are characterized in that they are typically larger than tablets which are intended to be swallowed; for example typically the total weight of such a tablet is at least 1 g and typically the minimum distance across the center of the largest face of the tablet is at least 10 mm, e.g. in the range 10–20 mm, and is suitably at least 15 mm. For example such a tablet can have a square cross-section wherein the sides of the square are at least 10 mm in length or it can be circular in cross-section such that the diameter of the circle is at least 10 mm.

Alternatively, or additionally, chewable tablets typically are characterized in that they contain flavouring and/or sweetening agents. In the present context, the term sweetening agents is intended to mean sweeteners other than sweet-tasting sugars, sugar alcohols and oligo- and polysaccharides, although such substances can also be included in the tablets. Thus, for example it is intended to refer to sweeteners such as ammonium glycyrrhizinate, and artificial sweeteners such as sodium cyclamate, sodium saccharinate and aspartame.

Flavouring agents can be natural in origin or synthetically obtained and can be employed to impart a variety of different tastes to the tablet, for example butterscotch, aniseed, mint and various fruit flavours or combinations thereof. Such flavouring agents are well known in the art of pharmacy and need not be described in detail here.

Chewable tablets are generally uncoated, i.e. they do not usually have a surface coating of a release-retarding or controlling substance.

The term insoluble as used herein refers to the definition in the U.S. Pharmacopoeia National Formulary USP XXI, 1985, whereby 10,000 or more parts of solvent are required to dissolve 1 part of solute.

Suitably the hygroscopic substance has the ability to absorb at least 5% by weight (relative to its own weight) of water in an atmosphere of 90% humidity. More usually it will have the ability to absorb about 10% or more, by weight, of water.

The water-insoluble hygroscopic excipient is suitably an organic substance and is preferably polymeric in nature; for example it can be a polysaccharide. Typically the hygroscopic excipient is chosen from the group of substances comprising underivatised celluloses such as powdered celluloses and microcrystalline celluloses; derivatised celluloses such as cross-linked carboxymethylcelluloses, e.g. the sodium and calcium cross-linked carboxymethylcelluloses; sodium starch glycolate and cross-linked polyvinylpyrrolidone.

Powdered cellulose is defined in the U.S. Pharmacopoeia National Formulary USP XXI (1985), page 1547, as being a purified, mechanically disintegrated cellulose prepared by processing alpha cellulose obtained as a pulp from fibrous plant materials. It is described as containing not less than 97.0% and not more than 102.0% of cellulose calculated on the dried basis.

Microcrystalline cellulose is defined in the U.S. Pharmacopoeia National Formulary USP XXI (1985), page 1546, as being partially depolymerised cellulose obtained by treating fibrous plant material-derived alpha cellulose with mineral acids. As with the powdered cellulose, it is described as containing 97.0–102.0% of cellulose calculated on the dried basis.

Particular examples of celluloses are microcrystalline celluloses such as Emcocel TM, (supplied by Edward Mendell of New York) and Avicel TM (supplied by FMC Corporation of Philadelphia, PA). Particular grades of Avicel TM include Avicel PH 103, Avicel PH 101 and Avicel PH 105. Further examples of celluloses are powdered celluloses such as Elcema TM (supplied by Degussa of Frankfurt).

Examples of cross-linked carboxymethylcelluloses (croscarmelloses) include the sodium salt Ac—Di—Sol and the calcium salt ECG 505 (both supplied by FMC Corporation).

Examples of sodium starch glycolate include Explotab TM which is supplied by Edward Mendell of New York, see also U.S. Pat. No. 3,034,911; and an example of a cross-linked polyvinylpyrrolidone is Kollidon CL which is supplied by BASF of the Federal Republic of Germany.

The water-insoluble hygroscopic substance typically constitutes 7–13% (w/w), for example approximately 9% (w/w) of the total weight of the tablet. Usually it is particulate in nature and suitably substantially all of the particles of hygroscopic substance will be less than 300µ in size, and the particle size typically will be in the range 20–150µ, for example approximately 100µ.

The therapeutically active substance can be any such substance which is capable of being administered orally but the compositions of the present invention are particularly advantageous when the substance has at least very slight solubility in water, i.e. it is soluble to the extent of at least 1 part in 10,000 parts of water.

Examples of therapeutically active substances which can be included in the compositions of the present invention include histamine $H_2$-receptor antagonists and substances, such as paracetamol, which typically require relatively high dosages in order to achieve the desired therapeutic effect.

Examples of $H_2$-antagonists include cimetidine, ranitidine, famotidine, nizatidine and roxatidine.

The compositions of the present invention are particularly useful for substances which have an unpalatable taste, for example a bitter taste. Such substances include, for example, cimetidine, ranitidine and paracetamol.

The therapeutically active substance can be granulated in accordance with standard pharmaceutical techniques; thus it can be mixed with a solution of a binding agent in a conventional mixing device or it can be subjected to fluidised bed granulation methods as known in the art.

In a second aspect, the present invention provides a solid pharmaceutical composition comprising cimetidine-containing granules, and an extragranular water-insoluble hygroscopic excipient in an amount of 5% to 15% (w/w) of the composition.

The composition typically contains 7–3% by weight of the hygroscopic excipient, for example approximately 9%.

The water-insoluble hygroscopic excipients are characterized as described hereinabove and particular examples of such excipients and their physical characteristics, e.g. particle size, are also as described hereinabove.

Preferred excipients for use in combination with cimetidine include particulate underivatised celluloses such as microcrystalline and powdered celluloses, e.g. the Avicels.

The granules of cimetidine can comprise an additional taste-masking agent. For example, the granules can be formed from a mixture of cimetidine and Eudragit E as described in European patent applications numbers 88304008.1and 88304007.3.

Particular dosage forms in accordance with the present invention are chewable tablets. Such tablets normally contain at least 75 mg of cimetidine. As a maximum the tablet will not normally contain more than 800 mg of cimetidine. Preferably it contains 100 or 200 mg of cimetidine.

The chewable tablets of the present invention can also contain solid diluents such as sugars and sugar alcohols, for example lactose, xylitol, sorbitol and mannitol. Where desired additional sweeteners can be added, for example ammonium glycyrrhizinate, sodium cyclamate, sodium saccharinate and aspartame as well as flavours and additional taste maskers, for example sodium chloride and Contramarum.

The tablets can also contain other standard tableting excipients; for example a disintegrant. It will be appreciated that when the disintegrant is a cross-linked carboxymethylcellulose, sodium starch glycolate, cross-linked polyvinylpyrrolidone, or like substance, it can also function as an extragranular, hygroscopic, water-insoluble excipient as defined hereinabove.

In one particular embodiment of the invention, there is provided a chewable tablet comprising granules containing a total of approximately 200 mg of cimetidine, the amount of cimetidine corresponding to approximately 12.5% by weight of the tablet; approximately 70% (w/w) lactose and/or sorbitol, and, as hygroscopic water-insoluble excipients, approximately 2.5% (w/w) croscarmellose sodium and approximately 9.5% microcrystalline cellulose.

The cimetidine compositions of the invention can also contain a hydroxide or carbonate antacid. Examples of suitable antacids include aluminium hydroxide, magnesium hydroxide, magnesium carbonate, calcium carbonate and co-dried gels for example aluminium hydroxide-magnesium carbonate co-dried gel. In practice the quantity of antacid is between 5 milli-equivalents per tablet and 30 milli-equivalents, typically approximately 14 milli-equivalents.

Where the tablet contains an antacid, preferably the antacid is pre-compressed or granulated before it is mixed with the cimetidine granules, for example as described in European Patent Application Number 88304008.1 (Publication No. 0 294 933) and as described in Example 1 of this application.

The granules can be sieved to remove fine particles and larger particles. Preferably the granules pass through a 1.4 mm sieve but are retained by a 0.2 mm sieve.

The antacid can be pre-compressed or granulated by standard methods.

The following Examples illustrate the invention.

EXAMPLE 1

200 mg. Cimetidine/Antacid Chewable Tablet

| Ingredient | mg/tablet | % w/w |
| --- | --- | --- |
| Cimetidine Premix Granules | | |
| Cimetidine | 200.0 | 90.9 |
| Eudragit E100 | 20.0 | 9.1 |
| Antacid (Al/Mg) Granules | | |
| Sorbitol: Direct Compression Grade | 590.0 | 34.01 |
| Lactose: Direct Compression Grade | | |
| Spray dried | 325.0 | 18.73 |
| Crystalline | 325.0 | 18.73 |
| Dried Aluminium Hydroxide Gel | 250.0 | 14.41 |
| Magnesium Hydroxide | 200.0 | 11.53 |
| Croscarmellose Sodium Type A+ | 30.0 | 1.73 |
| Magnesium Stearate | 15.0 | 0.86 |
| | 1735.0 | 100.00 |
| Tableting Mix for Compression | | |
| Cimetidine Premix Granules | 220.0 | |
| Antacid (Al/Mg) Granules | 1735.0 | |
| Microcrystalline Cellulose (Avicel PH102)+ | 200.0 | |
| Aspartame | 10.0 | |
| Aniseed | 20.0 | |
| Butterscotch | 20.0 | |
| Magnesium Stearate | 15.0 | |
| TOTAL | 2220.0 | |

+Croscarmellose Sodium Type A and Avicel PH102 can both be obtained from the FMC Corporation, Philadelphia PA.

Process Description

A 40% (w/w) solution of the Eudragit E100 in methylene chloride was added with mixing to the cimetidine and blended until granules were formed. The resulting granules were dried and then sieved through a 16 mesh screen.

The aluminium hydroxide, magnesium hydroxide and other ingredients for the antacid granules were sieved through a 12 mesh (1.4 mm) screen and mixed together. The resulting mix was compressed on a rotary tablet press and the resulting compacts were milled using a 12 mesh screen.

The cimetidine granules, antacid granules and extragranular excipients were put into a cone blender and mixed thoroughly. The resulting mix was discharged from the blender and compressed on a suitable rotary tablet press fitted with the appropriate punches.

EXAMPLE 2

200 mg. Cimetidine Chewable Tablet

| Ingredient | mg/tablet | % w/w |
| --- | --- | --- |
| Cimetidine | 200.0 | 12.7 |
| Eudragit E100 | 20.0 | 1.3 |
| Sorbitol: Direct Compression Grade | 600.0 | 38.0 |
| Lactose: Direct Compression Grade | 500.0 | 31.6 |
| Croscarmellose Sodium Type A | 40.0 | 2.5 |
| Aspartame | 10.0 | 0.6 |
| Aniseed Flavouring | 20.0 | 1.3 |
| Butterscotch Flavouring | 20.0 | 1.3 |
| Magnesium Stearate | 20.0 | 1.3 |
| Microcrystalline Cellulose (Avicel PH102) | 150.0 | 9.5 |
| | 1580.0 | |

The cimetidine and Eudragit E100 were granulated in the manner described in Example 1 and the resulting granules were compressed together with the remaining ingredients to form tablets.

We claim:

1. A pharmaceutical chewable tablet composition comprising:
   (i) granules containing a non-toxic effective amount of a histamine $H_2$ antagonist and
   (ii) an admixture of an extragranular water insoluble hygroscopic excipient in an amount of 5 % to 15 % by weight of the tablet wherein the hygroscopic excipient is selected from the group of substances consisting of microcrystalline cellulose, powdered cellulose, sodium starch glycolate and cross-linked polyvinylpyrrolidone.

2. A composition according to claim 1 wherein the amount of hygroscopic excipient is in the range of 7-13% by weight of the tablet.

3. A composition according to claim 2 wherein the amount of excipient is approximately 9% by weight of the tablet.

4. A method of masking the taste of a histamine $H_2$ receptor antagonist in a pharmaceutical chewable tablet composition comprising:
   (i) forming granules containing a non-toxic therapeutically effective amount of the histamine $H_2$ receptor antagonist;
   (ii) mixing an admixture of an extragranular water-insoluble hygroscopic excipient selected from the group of substances consisting of microcrystalline cellulose, powdered cellulose, sodium starch glycolate and cross-linked polyvinylpyrrolidone in an amount of 5% to 15% by weight of the total weight of the tablet with said granules; and
   (iii) compressing into a chewable tablet.

5. The method of claim 4 wherein the histamine $H_2$-receptor antagonist is selected from the group consisting of ranitidine, famotidine, cimetidine, nizatidine and roxatidine.

6. A solid pharmaceutical composition comprising granules containing a non-toxic therapeutically effective amount of cimetidine and an admixture of an extragranular water-insoluble hygroscopic excipient in an amount of 5% to 15% (w/w) of the composition wherein the hygroscopic excipient is selected from the group of substances consisting of microcrystalline cellulose, powdered cellulose, sodium starch glycolate, and cross-linked polyvinylpyrrolidone.

7. A composition according to claim 6 wherein the hygroscopic excipient is microcrystalline cellulose or powdered cellulose.

8. A composition according to claim 7 wherein the cellulose comprises particles, substantially none of which have a size greater than 300μ.

9. A composition according to claim 6 which contains an antacid.

10. A pharmaceutical chewable tablet composition comprising granules containing oimetidine and, as extragranular hygroscopic water-insoluble excipients, croscarmellose sodium and microcrystalline cellulose, said croscarmellose sodium and microcrystalline cellulose together constituting from 5% (w/w) to 15% (w/w) of the tablet.

11. A composition according to claim 10 wherein the cimetidine is present in an amount from 75 mg to about 200 mg.

12. A composition according to claim 10 wherein the croscarmellose constitutes about 2.5% (w/w) of the tablet and the microcrystalline cellulose constitutes about 9.5% (w/w) of the tablet.

13. The composition according to claim 1 wherein the histamine $H_2$-receptor antagonist is selected from the group consisting of ranitidine, famotidiine, cimetidine, nizatidine and roxatidine.

14. A pharmaceutical chewable tablet composition comprising:
   (i) granules containing a non-toxic therapeutically effective amount of a histamine $H_2$ receptor antagonist and
   (ii) an admixture of a taste-masking extragranular water-insoluble hygroscopic excipient selected from the group of substances consisting of microcrystalline cellulose, powdered cellulose, sodium starch glycolate and cross-linked polyvinylpyrrolidone in an amount of 5% to 15% by weight of the total weight of the tablet.

15. The composition of claim 1 wherein the therapeutically active substance is soluble in water in a ratio of 1:10,000 parts water.

16. The method of claim 5 wherein the histamine $H_2$-receptor antagonist is cimetidine.

17. The method of claim 4 wherein the hygroscopic excipient is microcrystalline cellulose or powdered cellulose.

* * * * *